United States Patent
Franklin (10) Patent No.: US 10,232,981 B1
(45) Date of Patent: Mar. 19, 2019

(54) TWO SIDED, MULTI-CUPPED FLUID HOLDER

(71) Applicant: Travis Franklin, Sarasota, FL (US)

(72) Inventor: Travis Franklin, Sarasota, FL (US)

(*) Notice: Subject to any disclaimer, the term of this patent is extended or adjusted under 35 U.S.C. 154(b) by 382 days.

(21) Appl. No.: 15/140,634

(22) Filed: Apr. 28, 2016

(51) Int. Cl.
| B65D 21/00 | (2006.01) |
| B65D 21/08 | (2006.01) |
| B65D 21/02 | (2006.01) |
| B65D 85/00 | (2006.01) |

(52) U.S. Cl.
CPC ......... B65D 21/08 (2013.01); B65D 21/0204 (2013.01); B65D 85/70 (2013.01)

(58) Field of Classification Search
CPC .... B65D 21/08; B65D 21/0204; B65D 85/70; B65D 1/04
See application file for complete search history.

(56) References Cited

U.S. PATENT DOCUMENTS

| 1,218,663 | A | * | 3/1917 | James | B43L 25/002 15/257.074 |
| 2,611,499 | A | * | 9/1952 | Mayer | B65D 1/10 215/6 |
| D214,745 | S | * | 7/1969 | Walker | 446/127 |
| 4,117,948 | A | * | 10/1978 | Collins | A47G 19/00 220/23.83 |
| 4,764,143 | A | * | 8/1988 | Gat | A63H 33/105 446/102 |
| 5,503,288 | A | * | 4/1996 | Conconi | B65D 21/0204 220/23.4 |
| D370,034 | S | * | 5/1996 | Kipfer | D21/386 |
| 8,985,366 | B2 | | 3/2015 | Barth | |
| D753,767 | S | * | 4/2016 | Blette | D19/104 |
| 2005/0189243 | A1 | * | 9/2005 | Manabe | B65D 21/0204 206/139 |
| 2009/0084690 | A1 | * | 4/2009 | Bressler | B65D 11/02 206/63.5 |
| 2011/0108513 | A1 | * | 5/2011 | Peter | B65D 21/0204 215/376 |
| 2012/0118848 | A1 | * | 5/2012 | Hendrickson | B65D 21/0204 215/40 |

* cited by examiner

Primary Examiner — Anthony Stashick
Assistant Examiner — James Way
(74) Attorney, Agent, or Firm — Edward P. Dutkiewicz (57) ABSTRACT

A two-sized, multi-cupped fluid holder having an upper end a plurality of hexagonally shaped upper recesses therein. There is also a lower end, with the lower end having a plurality of hexagonally shaped lower recesses therein. There is a side wall having a front surface and a back surface. The side wall front surface having at least one pair of outwardly projecting ridges. The side wall back surface having at least one pair of inwardly projecting grooves. The ridges and the grooves a first set being configured to mate with and receive the ridges and groves of another set.

18 Claims, 4 Drawing Sheets

TWO SIDED, MULTI-CUPPED FLUID HOLDER

BACKGROUND OF THE INVENTION

RULE 1.78(F) (1) DISCLOSURE

The Applicant has not submitted a related pending or patented non-provisional application within two months of the filing date of this present application. The invention is made by a single inventor, so there are no other inventors to be disclosed. This application is not under assignment to any other person or entity at this time.

FIELD OF THE INVENTION

The present invention relates to a two sided, multi-cupped fluid holder and more particularly pertains to a tattoo ink holder which has two sides and two volumes.

DESCRIPTION OF THE PRIOR ART

The use of cups to hold tattoo ink is known in the prior art. More specifically, cups to hold tattoo ink previously devised and utilized for the purpose of containing ink for tattooing are known to consist basically of familiar, expected, and obvious structural configurations, notwithstanding the number of designs encompassed by the prior art which has been developed for the fulfillment of countless objectives and requirements.

While the prior art devices fulfill their respective, particular objectives and requirements, the prior art does not describe two sided, multi-cupped fluid holder that provides a tattoo ink holder which has two sides and two volumes.

In this respect, the two sided, multi-cupped fluid holder, according to the present invention, substantially departs from the conventional concepts and designs of the prior art, and in doing so provides an apparatus primarily developed for the purpose of providing a tattoo ink holder which has two sides and two volumes.

Therefore, it can be appreciated that there exists a continuing need for a new and improved two sided, multi-cupped fluid holder, which can be used as a tattoo ink holder, which has two sides and two volumes. In this regard, the present invention substantially fulfills this need.

SUMMARY OF THE INVENTION

In view of the foregoing disadvantages inherent in the known types of cups to hold tattoo ink now present in the prior art, the present invention provides an improved two sided, multi-cupped fluid holder. As such, the general purpose of the present invention, which will be described subsequently in greater detail, is to provide a new and improved two sided, multi-cupped fluid holder which has all the advantages of the prior art and none of the disadvantages.

To attain this, the present invention essentially comprises a two-sized, multi-cupped, fluid holder, comprising several components, in combination.

The fluid holder has an upper end. The upper end forms an upper surface in an upper end plane. The upper surface has a plurality of hexagonally shaped upper recesses therein. Each of the hexagonally shaped upper recesses has an upper innermost surface, forming the extent and volume of each of the upper recesses. Each hexagonally shaped upper recess has an opening there into. Each of the hexagonally shaped upper recesses is surrounded by an hexagonally shaped upper wall. Each hexagonally shaped upper wall has a first outermost cross sectional area. Each hexagonally shaped upper wall has an upper extent and a lower extent. Each hexagonally shaped upper wall has a first thickness. The hexagonally shaped solid upper wall divides each of the upper surface hexagonally shaped upper recesses. Each upper surface hexagonally shaped upper recess has a separate and generally equal volume, being a first upper end volume. There is an upper top slot which is located between each of the hexagonally shaped upper walls.

There is a lower end. The lower end forms a lower surface in a lower end plane. The lower surface has a plurality of hexagonally shaped lower recesses therein. Each of the hexagonally shaped lower recesses has an innermost surface which forms the extent and volume of each of the lower recesses. Each hexagonally shaped lower recess has an opening there into.

Each of the hexagonally shaped lower recesses is surrounded by a solid hexagonally shaped lower wall. Each hexagonally shaped lower wall has a second outermost cross sectional area. Each hexagonally shaped lower wall has an upper extent and a lower extent. Each hexagonally shaped lower wall has a second thickness. The hexagonally shaped solid lower wall divides each of the lower surface hexagonally shaped upper recesses. The hexagonally shaped lower recesses each have a separate, and generally equal, volume, being a second lower end volume. There is a lower bottom slot which is located between each of the hexagonally shaped lower walls. The first upper end volume is greater than the second lower end volume.

There is a side wall. The side wall has an upper portion, a middle portion, and a lower portion. The side wall has a front surface and the side wall has a back surface. The side wall has an upper extent and a lower extent. The front surface and the back surface of the side wall each are continuous with the other. The front surface of the side wall and the back surface of the side wall have a generally angular configuration.

The side wall middle portion has a third outermost cross sectional area. The side wall middle portion is continuous with the side wall middle portion, and has an upper extent and a lower extent. The side wall middle portion forms a continuous plurality of hexagonal shapes. The front surface of the middle portion of the side wall has at least one pair of outwardly projecting ridges. Each of the outwardly projecting ridges of the side wall middle portion has a generally rectilinear configuration. Each of the ridges is oriented in an upward and a downward direction. The upward and downward directions is generally perpendicular to the upper end plane and the lower end plane. Each of the pairs of ridges is located at approximately one hundred and twenty degrees relative to each other.

The back surface of the middle portion of the side wall has at least one pair of inwardly projecting grooves. Each of the grooves has a generally rectilinear configuration. Each of the grooves is oriented in an upward and a downward direction. The upward and downward directions are generally perpendicular to the upper end plane and the lower end plane. Each of the pairs of grooves is located at approximately one hundred and twenty degrees relative to each other. Each of the pairs of grooves is oriented and aligned so as to receive and mate with one of the pairs of ridges. The mating of the ridges of the front surface of a first fluid holder to the grooves of a second fluid holder is carried out by the sliding of each of the ridges into one of the grooves. The motion to effectuate the mating is an upward or downward direction of each set to be mated.

The side wall upper portion has a fourth outermost cross sectional area. The side wall upper portion is continuous. The side wall upper portion has an upper extent and a lower extent. The side wall upper portion forms a plurality of hexagonal shapes. The upper top slot of the upper end is also located between each of the hexagonally shaped upper walls. The side wall upper portion also is continuous with the hexagonally shaped upper wall of the upper end. The side wall upper portion upper extent and the lower extent of the hexagonally shaped upper wall form an inward step which is located between the hexagonally shaped upper wall of the upper end and the side wall upper portion.

The side wall lower portion has a fifth outermost cross sectional area. The side wall lower portion is continuous. The side wall lower portion has an upper extent and a lower extent. The side wall lower portion forms a plurality of hexagonal shapes. The lower bottom slot of the lower end is also located between each of the hexagonally shaped lower walls. The side wall lower portion is also continuous with the hexagonally shaped lower wall of the lower end. The side wall lower portion lower extent and the upper extent of the hexagonally shaped lower wall forms an inward step which is located between the hexagonally shaped lower wall of the lower end and the side wall lower portion. The side wall lower portion has at least one downwardly projecting, generally trapezoidally shaped extension.

The two-sized, multi-cupped fluid holder is fabricated of a generally rigid material.

The third cross sectional area is greater than the second cross sectional area, the second cross sectional area is greater than the fourth cross sectional area, the first and fourth cross sectional areas is approximately equal and the fifth cross sectional area is less than the fourth cross sectional area.

Lastly, the upper wall first thickness is less than the lower wall second thickness.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. it is important, therefore, that the claims be regarded as including such equivalent constructions insofar as they do not depart from the spirit and scope of the present invention.

It is therefore an object of the present invention to provide a new and improved two sided, multi-cupped fluid holder which has all of the advantages of the prior art cups to hold tattoo ink and none of the disadvantages.

It is another object of the present invention to provide a new and improved two sided, multi-cupped fluid holder which may be easily and efficiently manufactured and marketed.

It is further object of the present invention to provide a new and improved two sided, multi-cupped fluid holder which is of durable and reliable constructions.

An even further object of the present invention is to provide a new and improved two sided, multi-cupped fluid holder which is susceptible of a low cost of manufacture with regard to both materials and labor, and which accordingly is then susceptible of low prices of sale to the consuming public, thereby making such two sided, multi-cupped fluid holder economically available to the buying public.

Even still another object of the present invention is to provide a two sided, multi-cupped fluid holder for a tattoo ink holder which has two sides and two volumes.

Lastly, it is an object of the present invention to provide a new and improved two-sized, multi-cupped fluid holder having an upper end a plurality of hexagonally shaped upper recesses therein. There is also a lower end, with the lower end having a plurality of hexagonally shaped lower recesses therein. There is a side wall having a front surface and a back surface. The side wall front surface having at least one pair of outwardly projecting ridges. The side wall back surface having at least one pair of inwardly projecting grooves. The ridges and the grooves a first set being configured to mate with and receive the ridges and groves of another fluid holder.

It should be understood that while the above-stated objects are goals which are sought to be achieved, such objects should not be construed as limiting or diminishing the scope of the claims herein made.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
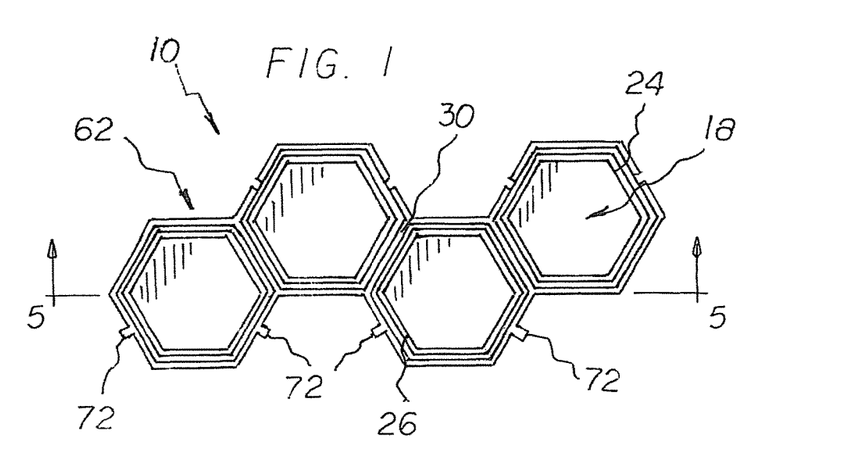
FIG. 1 is a plan view of the upper end of the fluid holder.

With reference now to the drawings, and in particular to FIG. 1 thereof, the preferred embodiment of the new and improved two sided, multi-cupped fluid holder embodying the principles and concepts of the present invention and generally designated by the reference numeral 10 will be described.

The present invention, the two sided, multi-cupped fluid holder 10 is comprised of a plurality of components. Such components in their broadest context include a first side with first volume recesses, a second side with second volume recesses, interlocking ridges and grooves. Such components are individually configured and correlated with respect to each other so as to attain the desired objective.

Herein described is a two-sized, multi-cupped fluid holder 10, comprising several components, in combination.

Figure 5:
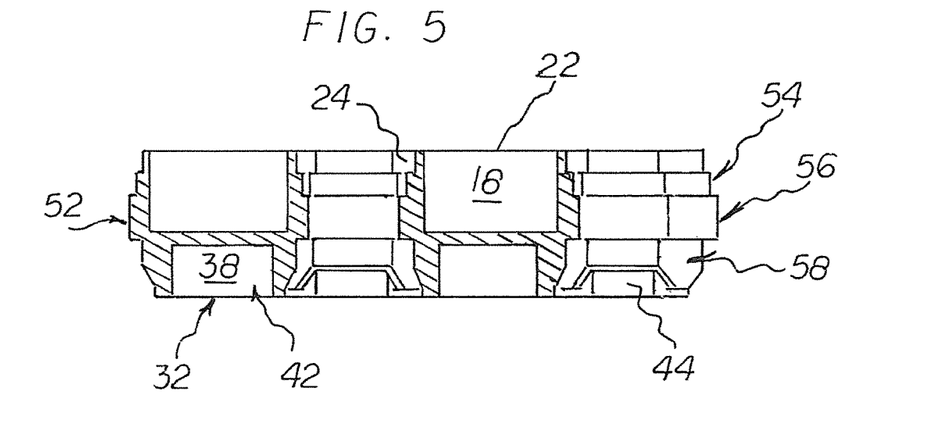
FIG. 5 is a cross sectional view taken along line 5-5 of FIG. 1.
Figure 7:
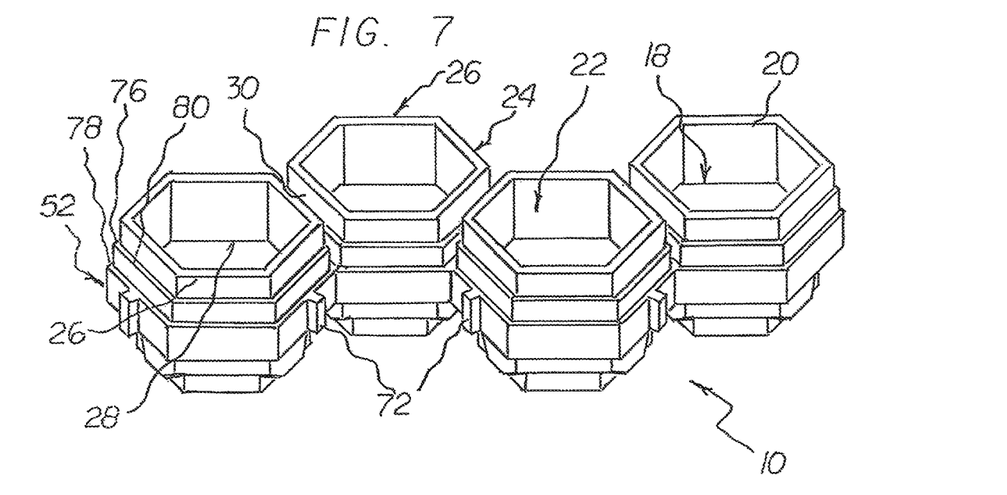
FIG. 7 is a upper perspective view of the upper end of the fluid holder, showing the centrally located recesses.

The fluid holder set has an upper end 12. The upper end forms an upper surface 14 in an upper end plane 16. The upper surface has a plurality of hexagonally shaped, centrally located, upper recesses 18 therein. Each of the hexagonally shaped upper recesses has an upper innermost surface 20, forming the uppermost extent and volume of each of the upper recesses. The upper recess opening lies in a first plane. Each hexagonally shaped upper recess has an opening 22 there into. Each of the hexagonally shaped upper recesses is surrounded by a solid hexagonally shaped upper wall 24. Each of the upper recesses have an upwardly directed opening. Each solid hexagonally shaped upper wall has a first outermost cross sectional area. Each solid hexagonally shaped upper wall has an upper extent 26 and a lower extent 28. Each solid hexagonally shaped upper wall has a first thickness. The hexagonally shaped solid upper wall divides each of the upper surface hexagonally shaped upper recesses. Each upper surface hexagonally shaped upper recess has a separate and generally equal volume, being a first upper end volume. There is an upper top slot 30 which is located between each of the hexagonally shaped upper walls. The slots aid in preventing dripping, or runoff, from contaminating the contents of adjacent, or nearby recesses.

Figure 4:
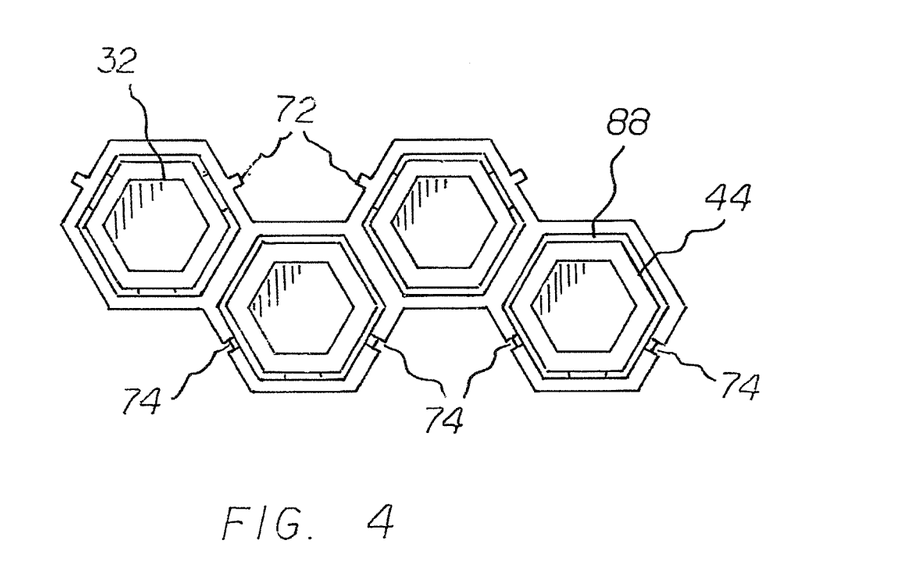
FIG. 4 is a plan view of the lower end of the fluid holder.
Figure 8:
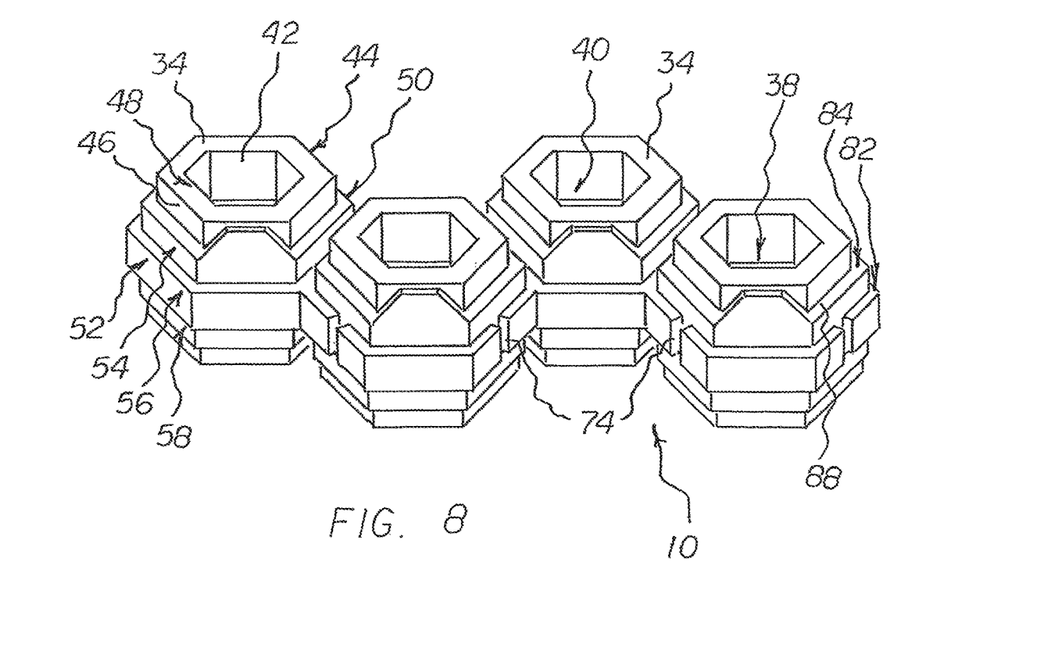
FIG. 8 is a lower perspective view of the lower end of the fluid holder showing the centrally located recesses.

There is a lower end 32. The lower end forms a lower surface 34 in a lower end plane 36. The lower end is located opposite of the upper end and lies in a second plane parallel to the upper end. The lower end is continuous with the upper end. The lower surface has a plurality of hexagonally shaped, centrally located, lower recesses 38 therein. Each of the hexagonally shaped lower recesses has an innermost surface 40 which forms the extent and volume of each of the lower recesses. Each hexagonally shaped lower recess has an opening 42 there into. Each of the lower end recesses openings is downwardly directed.

Each of the hexagonally shaped lower recesses is surrounded by a solid hexagonally shaped lower wall 44. Each hexagonally shaped lower wall has a second outermost cross sectional area. Each hexagonally shaped lower wall has an upper extent 46 and a lower extent 48. Each hexagonally shaped lower wall has a second thickness. The hexagonally shaped solid lower wall divides each of the lower surface hexagonally shaped upper recesses. The hexagonally shaped lower recesses each have a separate, and generally equal, volume, being a second lower end volume. There is a lower bottom slot 50 which is located between each of the hexagonally shaped lower walls. The first upper end volume is greater than the second lower end volume.

Figure 2:
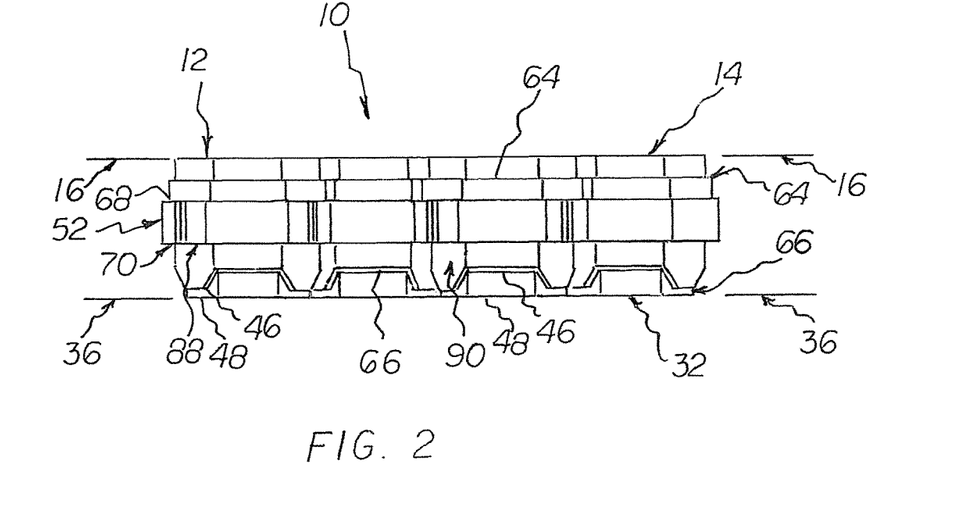
FIG. 2 is a side elevation view of the fluid holder.
Figure 3:
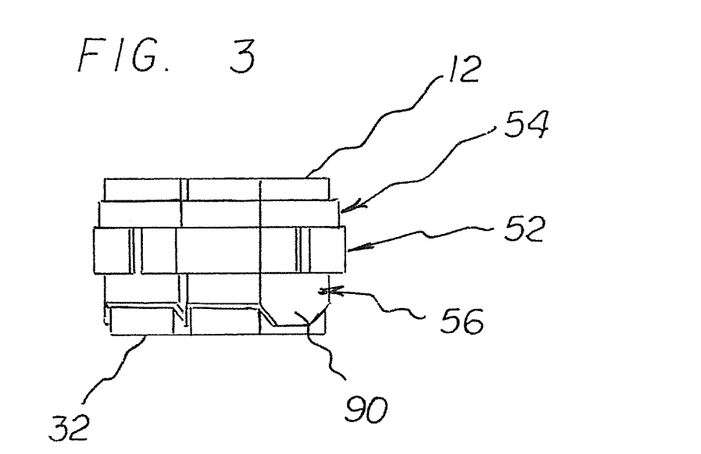
FIG. 3 is an end view of the fluid holder.

There is a side wall 52. The side wall is solid. The side wall has an upper portion 54, a middle portion 56, and a lower portion 58. The side wall has a front surface 60 and the side wall has a back surface 62. The side wall has an upper extent 64 and a lower extent 66. The front surface of the side wall and the back surface of the side wall are continuous with the other. The front surface of the side wall and the back surface of the side wall have a generally angular configuration.

The side wall middle portion has a third outermost cross sectional area. The side wall middle portion is continuous with the side wall middle portion, and has an upper extent 68 and a lower extent 70. The side wall middle portion forms a continuous plurality of hexagonal shapes. The front surface of the middle portion of the side wall has at least one pair of outwardly projecting ridges 72. Each of the outwardly projecting ridges of the side wall middle portion has a generally rectilinear configuration. Each of the ridges is oriented in an upward and a downward direction. The upward and downward directions is generally perpendicular to the upper end plane and the lower end plane. Each of the pairs of ridges is located at approximately one hundred and twenty degrees relative to each other.

The back surface of the middle portion of the side wall has at least one pair of inwardly projecting grooves 74. Each of the grooves has a generally rectilinear configuration. Each of the grooves is oriented in an upward and a downward direction. The upward and downward directions are generally perpendicular to the upper end plane and the lower end plane. Each of the pairs of grooves is located at approximately one hundred and twenty degrees relative to each other. Each of the pairs of grooves is oriented and aligned so as to receive and mate with one of the pairs of ridges. The mating of the ridges of the front surface of a first set to the grooves of a second set is carried out by the sliding of each of the ridges into one of the grooves. The motion to effectuate the mating is an upward, or downward, direction of each set to be mated, relative to the other.

The side wall upper portion has a fourth outermost cross sectional area. The side wall upper portion is continuous. The side wall upper portion has an upper extent 76 and a lower extent 78. The side wall upper portion forms a plurality of hexagonal shapes. The upper top slot of the upper end is also located between each of the hexagonally shaped upper walls. The side wall upper portion also is continuous with the hexagonally shaped upper wall of the upper end. The side wall upper portion upper extent and the lower extent of the hexagonally shaped upper wall form an inward step 80 which is located between the hexagonally shaped upper wall of the upper end and the side wall upper portion.

The side wall lower portion has a fifth outermost cross sectional area. The side wall lower portion is continuous. The side wall lower portion has an upper extent 82 and a lower extent 84. The side wall lower portion forms a plurality of hexagonal shapes. The lower bottom slot of the lower end is also located between each of the hexagonally shaped lower walls.

The side wall lower portion is also continuous with the hexagonally shaped lower wall of the lower end. The side wall lower portion lower extent and the upper extent of the hexagonally shaped lower wall forms an inward step 88 which is located between the hexagonally shaped lower wall of the lower end and the side wall lower portion. The side wall lower portion has at least one downwardly projecting, generally trapezoidally-shaped, extension 90. The function of the trapezpoindally-shaped, extension is to allow the stacking of the fluid holders. The added material of the extension allows the overlapping of the upper end on the lower end with the extension forming a snug fit. The purpose of stacking is that a tattoo artist may prepare inks for the final stages of the tattoo process. The artist may stack the fluid holders, effectively "capping" the inks he will use last in the tattoo process. The "capping" by stacking, prevents the ink from drying. This allows the tattoo artist to prepare all inks, and have them in one location, before coming into physical contact with a patron. This adds to the individual isolation which is required in preventing the spread of any contagion or disease, from customer to customer. This process "isolates" the customer, keeping all his or her ink supplies, and tattoo supplies, separate from anyone else.

The two-sized, multi-cupped fluid holder is fabricated of a generally rigid material.

The third cross sectional area is greater than the second cross sectional area, the second cross sectional area is greater than the fourth cross sectional area, the first and fourth cross sectional areas is approximately equal and the fifth cross sectional area is less than the fourth cross sectional area.

Lastly, the upper wall first thickness is less than the lower wall second thickness.

The present invention provides an advantage over the prior art. The two-sized, multi-cupped fluid holder is used for containing tattoo ink for use during the tattoo process. In use, the artist slips, that is, connects, two fluid holders together. This is done by mating the ridges and the grooves, and sliding a first fluid holder upwards, relative to the other, thereby engaging the ridges within the grooves. This orientation prevents the fluid holders from separating from one another, in that a user must move one upwards, relative to the other, so as to disengage the ridges and the grooves.

The fluid holder has two sizes of recesses, or fluid holders. There are, in the preferred embodiment, four fluid holders, or cups, of a first size, on one side of the fluid holder, and four fluid holders, or cups, of a second size on the opposite side of the fluid holder. The user is able to join together, or couple, several holders into one "sheet" of holders, or one configuration. The fluid holders, or cups, are adjacent to one another. The fluid holder cups, when joined to another holder, do not have to be oriented with all the same sized cup upwards, but the user may join holders in either orientation.

In describing this invention, the word "coupled" is used. By "coupled" is meant that the article or structure referred to is joined, either directly, or indirectly, to another article or structure. By "indirectly joined" is meant that there may be an intervening article or structure imposed between the two articles which are "coupled". "Directly joined" means that the two articles or structures are in contact with one another or are essentially continuous with one another.

By "adjacent" to a structure is meant that the location is near the identified structure.

Figure 6:
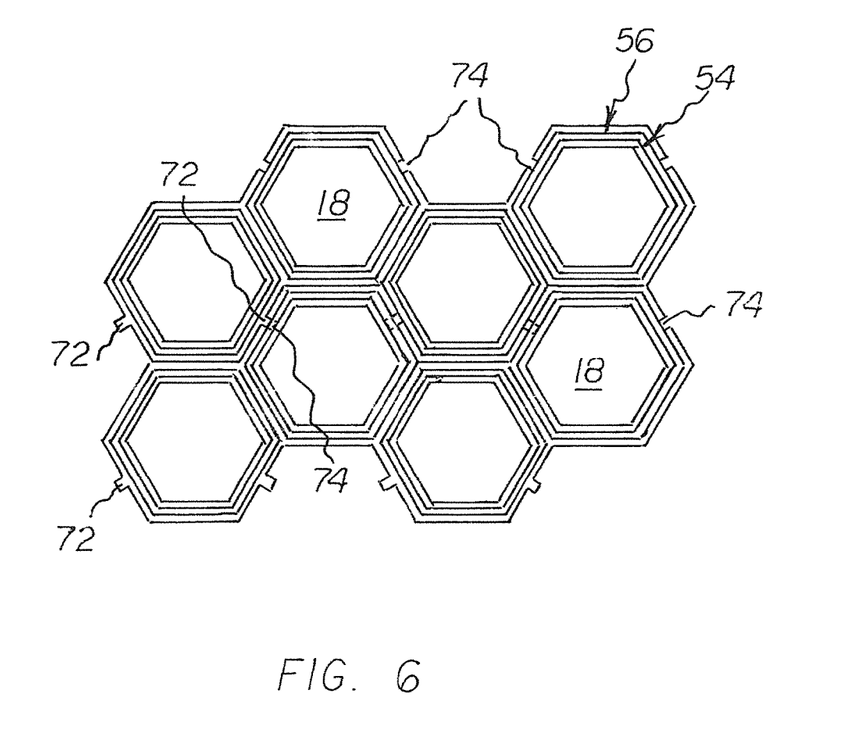
FIG. 6 is a plan view of the upper end showing two fluid holders coupled together using the ridges and the grooves.

When more than one holder is joined together, a "honeycomb-like" structure is attained, as shown in FIG. 6, wherein the upper cups, the larger cups, are shown joined together. The tattoo artist can locate the specific colors in proximity to one another by placing various colors of tattoo ink in the cups. The configuration of the cups being in a generally linear, or honeycomb, configuration helps the artist in using shading, wherein there are various amounts of ink added to a standard container, or cup, and then a diluent is added. This allows the artist to have, readily available, a "spectrum" of the same color, to assist in shading of tattoos in a convenient manner.

Another advantage to the artist is that the cups are uniform in size, wither the cup is the smaller or the larger. This allows an artist to replicate colors, by simply remembering, or making note of, the number of ink drops in a cup volume. This allows the artist to quantify the color sought, and attained so as to make further coloration more predictable, and replicable.

In that the cups are fixed in position, there is little, if any, potential for the mixing up of the shading sequence. Also, the smaller cups require less ink to attain a specific shade or color, which is more economical when only a small amount of ink is required for a specific skin art rendering. The fluid holder cups can be, as described, joined together, as a sheet, so that the risk of tipping is minimized, or eliminated, making the tattooing process more efficient, and economical.

The use of a single solid configuration makes the molding process more efficient. The steps in the side walls are formed by a perpendicular connector, but the molding process requires that the junctures of the steps, in connecting the various parts of the side wall, are generally rounded at the points of intersection. Corners, likewise, are generally rounded so as to allow easy extraction from the mold during the molding process.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A two-sized, multi-cupped fluid holder, comprising, in combination;

an upper end, with the upper end forming an upper surface in an upper end plane, the upper surface having a plurality of hexagonally shaped upper recesses therein with each of the hexagonally shaped upper recesses having an upper innermost surface forming an uppermost extent and a first volume of each of the upper recesses, the upper end recess uppermost extent being open and continuous along the entire upper innermost surface, each hexagonally shaped upper recess having an opening there into;

lower end, with the lower end forming a lower surface in a lower end plane, the lower surface having a plurality of hexagonally shaped lower recesses therein with each of the hexagonally shaped lower recesses having an innermost surface forming a lowermost extent and a second volume of each of the lower recesses, the lower end, recess lowermost extent being open and continuous along the entire lower innermost surface, each hexagonally shaped lower recess having an opening there into, the first volume being greater than the second volume;

the lower end and the upper end being located oppositely of each other, with the lower end and the upper end being continuous with each other, the lower end and the upper end lying in generally parallel planes;

a side wall, with the side wall haing an upper portion and a middle portion and a lower portion, the side wall having a front surface and the side wall having a back surface, the side wall having an upper extent and a lower extent, the front surface and the back surface of the side wall each being continuous with each other, and the front surface of the side wall and the back surface of the side wall having a generally angular configuration;

the front surface of the middle portion of the side wall having at least one pair of outwardly projecting ridges; and the back surface of the middle portion of the side wall having at least one pair of inwardly projeting grooves.

2. The two-sized, multi-cupped fluid holder, as described in claim 1, fluid holder further comprising;

each of the hexagonally shaped upper recesses being surrounded by an hexagonally shaped upperwall;

each of the hexagonally shaped lower recesses being surrounded by an hexagonally shaped lower wall;

each of the ridges of the side wall middle portion having a generally rectilinear configuration, with each of the ridges being oriented in an upward and a downward direction; and each of the grooves having a generally rectilinear configuration, with each of the grooves being oriented in an upward and a downward direction.

3. The two-sized, multi-cupped fluid holder, as described in claim. 2, with the fluid holder further comprising;

the hexagonally shaped solid upper wall dividing each of the upper surface hexagonally shaped upper recesses; and the hexagonally shaped solid lower wall dividing each of the lower surface hexagonally shaped lower recesses.

4. The two-sized, multi-cupped fluid holder, as described in claim 3, with the fluid holder further comprising;

each upper surface hexagonally shaped upper recess having a separate and generally equal volume, being the first upper end volume;

the hexagonally shaped lower recess having a separate and generally equal volume, being the second lower end volume;

the upward and downward directions being generally perpendcular to the upper end plane and the lower end plane.

5. The two-sized, multi-cupped fluid holder, as described in claim 4, with the fluid holder further comprising;

each hexagonally shaped upper wall having a first outermost cross sectional area; and each hexagonally shaped lower wall having a second outermost cross sectional area.

6. The two-sized, multi-cupped fluid holder, as described in claim 5, with the fluid holder further comprising;

each hexagonally shaped upper wall having an upper extent and a lower extent;

each hexagonally shaped lower wall having an upper extent and a lower extent;

each of the pairs of ridges being located at approximately one hundred and twenty degrees relative to each other; and each of the pairs of grooves being located at approximately one hundred and twenty degrees relative to each other.

7. The two-sized, multi-cupped fluid holder, as described in claim 6, with the fluid holder further comprising each of the pairs of grooves being oriented and aligned so as to receive and mate with one of the pairs of ridges, the mating of the ridges of the front surface of a first set to the grooves of a second set being carried out by the sliding of each of the ridges into one of the grooves.

8. The two-sized, multi-cupped fluid holder, as described in claim 7, with the fluid holder further comprising;

the side wall middle portion being continuous with, the side wall middle portion having an upper extent and a lower extent;

the side wall upper portion being continuous, the side wall upper portion having an upper extent and a lower extent; and the side wall lower portion being continuous, the side wall lower portion having an upper extent and a lower extent.

9. The two-sized, multi-cupped fluid holder, as described in claim 8, with the fluid holder further comprising;

an upper top slot being located between each of the hexagonally shaped upper walls;

lower bottom slot being located between each of the hexagonally shaped lower walls, with the first upper end volume being greater than the second lower end volume;

the side wall middle portion forming a continuous plurality of hexagonal shapes;

the side wall upper portion forming a plurality of hexagonal shapes, with the upper top slot of the upper end also being located between each of the hexagonally shaped upper walls; and the side wall lower portion forming a plurality of hexagonal shapes, with the lower bottom slot of the lower end also being located between each of the hexagonally shaped lower walls.

10. The two-sized, multi-cupped fluid holder, as described in claim 9, with the fluid holder further comprising;

each hexagonally shaped upper wall having a first thickness;

each hexagonally shaped lower wall having a second thickness;

the side wall middle portion having a third outermost cross sectional area;

the side wall upper portion having a fourth outermost cross sectional area; and the side, wall lower portion having a fifth outermost cross sectional area.

11. The two-sized, multi-cupped fluid holder, as described in claim 10, with the fluid holder further comprising;

the side wall upper portion also being continuous with the hexagonally shaped upper wall of the upper end, with side wall upper portion upper extent and the lower extent of the hexagonally shaped upper wall forming an inward step being located between the hexagonally shaped upper wall of the upper end and the side wall upper portion; and the side wall lower portion also being continuous with the hexagonally shaped lower wall of the lower end, with side wall lower portion lower-extent and the upper extent of the hexagonally shaped lower wall forming an inward step being located between the hexagonally shaped lower wall of the lower end and the side wall lower portion.

12. The two-sized, multi-cupped fluid holder, as described in claim 11, with the fluid holder further comprising the side wall lower portion having at least one downwardly projecting, generally trapezoidally shaped extension.

13. The two-sized, multi-cupped fluid holder, as described in claim 12, with the fluid holder further comprising the two-sized, multi-cupped fluid holder being fabricated of a generally rigid material.

14. The two-sized, multi-cupped fluid holder, as described in claim 13, with the fluid holder further comprising the third cross sectional area being greater than the second cross sectional area, the second cross sectional area being greater than the fourth cross sectional area, the first and fourth cross sectional areas being approximately equal and the fifth cross sectional area being less than the fourth cross sectional area.

15. The two-sized, multi-cupped fluid holder, as described in claim 14, with the fluid holder further comprising the upper wall first thickness being less than the lower wall second thickness.

16. A two-sized, multi-cupped fluid holder, Comprising, in combination;
   an upper end having a plurality of hexagonally shaped and centrally located upper recesses therein with the upper end recesses having a first volume, the upper end having an uppermost extent and an upper innermost surface, the upper end recess uppermost extent being open and continuous along the entire upper innermost surface;
   a lower end having a plurality of hexagonally shaped centrally located lower recesses therein with the lower end recesses having a second volume, the lower end recess having a lowermost extent and a lower innermost surface, the lowermost extent being open and continuous along the entirer lower innermost surface;
   the lower end and the upper end being located oppositely of each other, with the lower end and the upper end being continuous with each other, the lower end and the upper end lying in generally parallel planes;
   side wall having a front surface and a back surface, the front surface of the side wall having at least one pair of outwardly projecting ridges and the back surface of the side wall having at least one pair of inwardly projecting grooves.

17. The two-sized, multi-cupped fluid holder, as described in claim 16, with the fluid holder further comprising;
   an upper top slot being located between each of the upper end recesses;
   a lower bottom slot being located between each of the lower end recesses; and
   the upper end recess first volume being greater than the lower end recess second volume.

18. A fluid bolder, with the fluid holder comprising, in combination;
   an upper end having a hexagonally shaped and centrally located upper recess therein with the upper end recesses having a volume, the upper end having an upwardly directed opening;
   a lower end having a hexagonally shaped configuration, the a lower end having a downwardly directed opening;
   the lower end and the upper end being located oppositely of each other, with the lower end and the upper end being continuous with each other, the lower end and the upper end lying in generally parallel planes;
   a side wall having a front surface and a back surface, the front surface of the side wall having at least one outwardly projecting ridge and the back surface of the side wall having at least one inwardly projecting groove, the groove being configured to accept and mate with the ridge.

* * * * *